Figure 1:
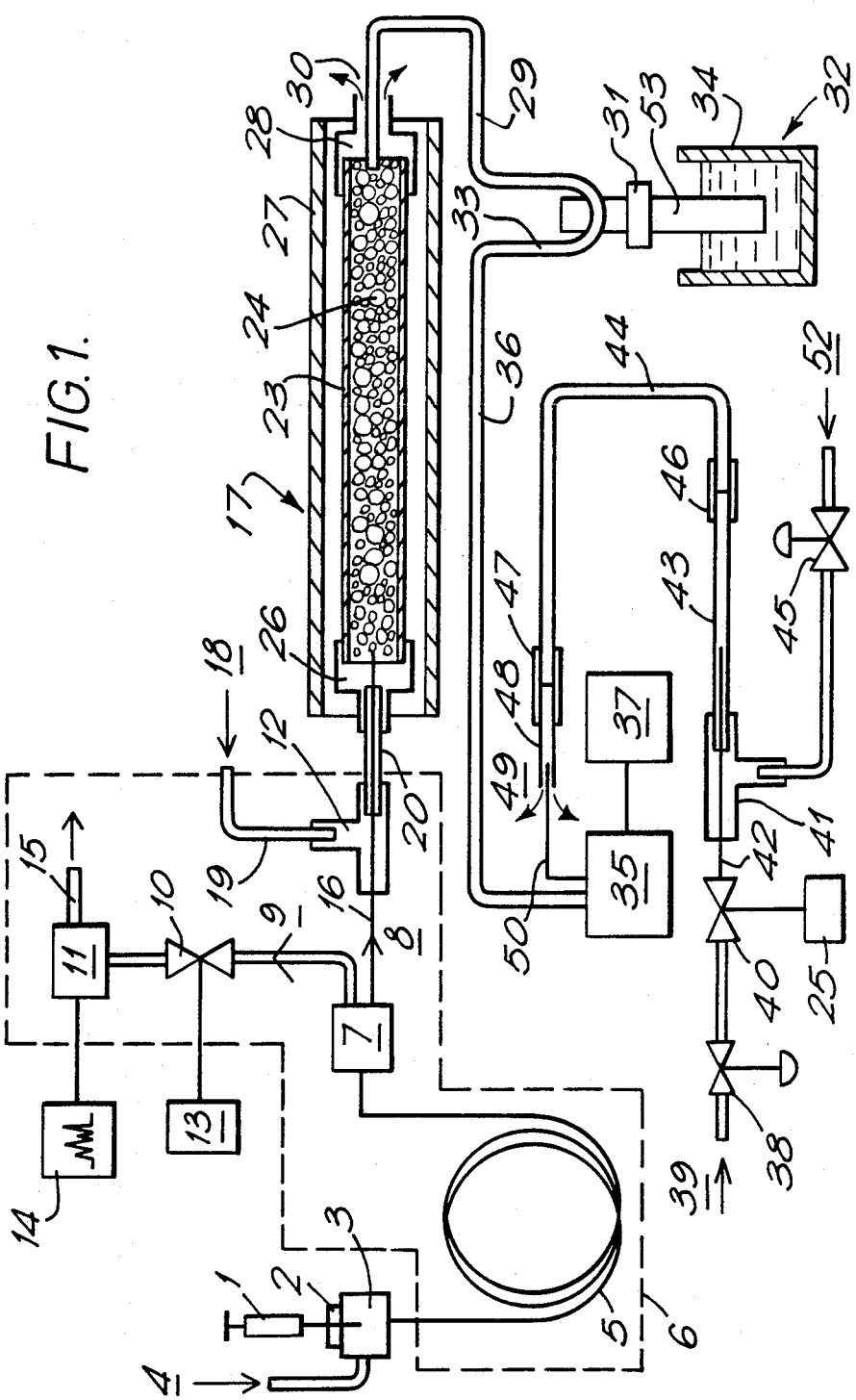

United States Patent [19]

Hall et al.

[11] Patent Number: 4,916,313
[45] Date of Patent: Apr. 10, 1990

[54] METHOD AND APPARATUS FOR THE DETERMINATION OF ISOTOPIC COMPOSITION

[75] Inventors: Keith Hall, Altrincham; Philip A. Freedman, Hartford; Elizabeth J. Jumeau, Leftwich, all of England; Roger Guilluy, St Bon et de Mure, France; Christiane Pachiaudi, Meyrieu, France; Jean P. Riou, Lyon, France

[73] Assignee: VG Instruments Group Limited, Crawley, England

[21] Appl. No.: 238,910

[22] Filed: Aug. 31, 1988

[30] Foreign Application Priority Data

Sep. 2, 1987 [GB] United Kingdom ............... 8720586

[51] Int. Cl.⁴ .......................................... B01D 59/44
[52] U.S. Cl. .................................. 250/282; 250/288; 436/173
[58] Field of Search ............... 250/282, 288, 288 A; 436/173

[56] References Cited

U.S. PATENT DOCUMENTS 4,641,541  2/1987  Sharp ................................ 250/288

OTHER PUBLICATIONS

Matthews et al., *Analytical Chemistry*, vol. 50, No. 11, Sep. 1978, pp. 1465–1473.
McKinney et al., *The Review of Scientific Instruments*, vol. 21, No. 8, Aug. 1950, pp. 724–730.
Santrock, Hayes, Anal. Chem., 1987, vol. 59(1), pp. 119–127.
Barrie, Bricout and Koziet, Biomed. Mass Spectrom., 1984, vol. 11(11), pp. 583–588.
Matthews Hays, Anal. Chem., 1976, vol. 48(9), pp. 1375–1382.
Gilmour, Swart, Pillinger, Org. Geochem., 1984, vol. 6, pp. 665–670.
Sano, Yotsui, Abe, Sasaki, Biomed. Mass Spectrom., 1976, vol. 3, pp. 1–3.
Preston, Owens, Biomed, Mass Spectrom., 1985, vol. 12(9), pp. 510–513.
Hays, 31st an. Confr. on Mass Spectrom. and Allied Topics, Boston, U.S.A., May 1983, pp. 450–453.
Preston, Owens, Analyst, 1983, vol. 108, pp. 971–977.

*Primary Examiner*—Jack I. Berman
*Attorney, Agent, or Firm*—Chilton, Alix & Van Kirk

[57] ABSTRACT

The invention provides a method and apparatus for the mass spectrometric determination of the isotopic composition of an element comprised in a sample by gas chromatography-isotopic ratio mass spectrometry. As a sample elutes from the column of the gas chromatograph it enters a sample conversion means which converts the element to an analysis gas (a gas comprising the element in elemental form or in the form of a simple compound, e.g. nitrogen or carbon dioxide) which is admitted into the mass spectrometer only during a second time interval corresponding to the elution of the peak containing the sample from the column. One or more calibration samples of a reference gas are admitted into the spectrometer during first time intervals which do not overlap the second time interval, thereby minimizing the contribution of the analysis gas to the reference gas mass analysis, and vice versa. Various devices are provided to minimize disturbance to the flow of gas into the spectrometer during practice of the method.

24 Claims, 2 Drawing Sheets

METHOD AND APPARATUS FOR THE DETERMINATION OF ISOTOPIC COMPOSITION

This invention relates to an isotopic-ratio analyzer for determining the precise isotopic composition of the elements in a sample, and in particular to an analyzer comprising a gas chromatograph and an isotopic-ratio mass spectrometer. It is particularly suitable for determining the isotopic composition of components in a mixture.

Two methods are known for the mass spectrometric determination of the isotopic composition of elements comprised in an organic compound present in a mixture. In the first method, a conventional gas chromatograph-mass spectrometer is employed. Samples are injected on to the gas-chromatographic column and the mass spectrometer is used in the selective ion recording mode to monitor peaks which are characteristic of the isotopes concerned as the peak of interest elutes from the chromatograph. The precision obtainable is limited by the presence of materials with different isotopic compositions at each of the masses monitored and also by the stability of the spectrometer.

The second method (known as isotopic-ratio gas-chromatography mass spectrometry, IRGCMS) is to convert the organic compounds to an analysis gas (that is, a gas comprising the element in elemental form or in the form of a simple compound, eg, $CO_2$ or $N_2$, etc) as they elute from the chromatograph and to analyze the isotopic composition of the analysis gas produced using a multi-collector isotopic-ratio mass spectrometer which is adapted for its analysis. This method is in principle capable of greater accuracy than the first method, but accuracy is limited in prior apparatus by a variety of factors associated with the sample conversion process and the interface to the spectrometer. Typical prior interfaces for IRGCMS are described by Matthews and Hayes in Analytical Chemistry, 1978, vol. 50(11) pp 1465 and Barrie, Bricout and Koziet, Biomed. Mass Spectrom, 1984, vol. 11(11) pp 583. Matthews and Hayes used a conventional packed G.C. column, the effluent from which was passed over a heated catalyst (cupric oxide) to convert carbon present in the sample into $CO_2$, and then through a trap containing magnesium perchlorate to remove water. The effluent from the trap was admitted into a dual-collector isotopic-ratio mass spectrometer adapted for $CO_2$ analysis and to determine the $^{13}C/^{12}C$ ratio. A dump valve was also provided to allow the solvent to elute from the chromatograph without it passing over the catalyst or into the spectrometer. Nitrogen isotopes were also determined by reducing with a heated copper catalyst the nitrogen oxides formed from the nitrogen present in the sample and analyzing the nitrogen so formed. An additional trap was used to remove $CO_2$ which would otherwise interfere with the mass spectrometric determination.

Barrie, et al, employed a fused silica capillary G.C. column in a similar apparatus, thereby eliminating the need for the jet separator used by Matthews and Hayes. In its place a conventional open split, purged with helium, was used to ensure the correct gas flow into the spectrometer and that this flow was independent of changes in the G.C. flow rate. Cobaltic oxide ($Co_3O_4$) was used as a catalyst. This method gave improved accuracy but was still not high enough to allow IRGCMS to be used in a routine way for stable isotope measurements for biomedical purposes.

It is the object of the present invention to provide an improved method of determining the isotopic composition of an element in a sample, especially when the sample is a mixture, and also to provide improved apparatus for carrying out that method.

In accordance with this objective there is provided a method of determining the isotopic composition of an element comprised in a sample, said method comprising:

a) passing a carrier gas through a gas chromatographic column and introducing said sample on to said column;

b) converting at least some of said sample present in the effluent from said column into an analysis gas (that is, a gas comprising said element in elemental form or the form of a simple compound, eg, nitrogen or carbon dioxide);

c) introducing one or more calibration samples of a reference gas containing said element into said spectrometer during at least one first time interval;

d) allowing carrier gas which has passed through said column to flow into said mass spectrometer only during at least one second time interval, outside the or each said first time interval, at least some of said analysis gas being allowed into said mass spectrometer during a said second time interval; and e) determining the isotopic composition of said element in said analysis gas from outputs of said mass spectrometer indicative of said element in said analysis gas and said reference gas.

Each of the second time intervals is typically selected to allow the analysis of a sample containing the element as it elutes from the gas chromatographic column and is converted into the analysis gas. Thus each time interval will preferably commence just prior to the time the eluting sample reaches the mass spectrometer and will terminate after substantially all of the eluting sample has passed into it. Obviously, the sample will be retained on the column for a certain time so that the start of the second time interval will not correspond with the time when a sample is introduced on to the column. A further time delay may also be introduced by the conversion of the sample into the analysis gas. If only one sample in a mixture is to be analyzed, then only one second time interval will be used, but if more than one sample is to be analyzed, several second time intervals may be selected, each corresponding to one of the samples eluting from the gas chromatographic column. Alternatively, at least one of the second time intervals may be extended to encompass two or more samples which elute close together.

Preferably each of the second time intervals should be such that at least some of the effluent from the gas chromatographic column is converted into analysis gas for substantially all of the time that the sample is eluting from the column, and such that at least some of the effluent after conversion is passed into the mass spectrometer for substantially all of the time there is analysis gas present in it. The outputs of the mass spectrometer indicative of at least two isotopes of the element may then be integrated for substantially all of the time the analysis gas is entering the spectrometer in order to determine the isotopic ratio. In this way the effects of isotopic fractionation of the sample by the chromatograph and/or the conversion process can be substantially eliminated.

According to the invention, at least one calibration sample of a reference gas is introduced into the mass spectrometer during a first time interval during which substantially no carrier gas which has passed through the chromatographic column is entering the mass spectrometer. Preferably the reference gas is of the same chemical composition as the analysis gas (eg, carbon dioxide for carbon isotopic ratio measurements), and is of known isotopic composition. The ratio measurements made on the reference gas are used to calibrate the mass spectrometer in a conventional waY. Providing that the reference gas is present in the spectrometer only when the analysis gas is not present, the reference gas can be introduced at any convenient point, for example as a pure gas directly into the mass spectrometer from a conventional inlet system. A preferred method of introducing the reference gas is in another flow of carrier gas into the mass spectrometer, as disclosed in our copending application Ser. No. 238,898 of even date herewith and claiming the priority of GB88113790 and GB8720586.

In order to facilitate the introduction of the reference gas the second time intervals should therefore be selected to be as short as possible, consistent with the requirements discussed above. This also minimizes contamination of the mass spectrometer and the inlet system.

Preferably only some of the effluent from the gas chromatographic column is passed into the mass spectrometer, and the remainder is vented at a substantially constant, eg, atmospheric, pressure. Further, a second flow of carrier gas may be added to the effluent from the column prior to the conversion of the sample into the analysis gas, and the venting of the remaining portion of the flow of carrier gas is carried out after the sample has been converted. This results in the pressure in the mass spectrometer remaining constant even if the flow of carrier gas through the chromatographic column is changed, thereby improving the stability of the spectrometer. The second flow of carrier gas may be selected so that the linear flow velocity of the carrier gas through the apparatus used to convert the sample is approximately the same as that through the column, thereby minimizing peak broadening.

In a preferred method, effluent from the gas chromatographic column is converted only when there is a sample present in it, so that contamination of the conversion apparatus is minimized and no materials due to column bleed will be present in the mass spectrometer when a calibration sample is being analyzed. This method is very easily implemented when a second flow of carrier gas is added as described above, necessitating only the diversion of the chromatographic column effluent prior to the point of the addition. The times during which the diversion should take place must be determined from knowledge of the retention time of the sample of interest and the delay introduced by the conversion process, which can be determined for example by prior experiment. The times during which the reference gas may be admitted are then determined so that the first and second time intervals as defined do not overlap.

According to another aspect, the invention provides apparatus for the determinaton of the isotopic composition of an element comprised in a sample, said apparatus comprising:

a) an isotopic ratio mass spectrometer adapted for the determination of the isotopic composition of an element comprised in a gas;

b) a gas chromatographic column through which a sample may be passed together with a carrier gas;

c) a sample conversion means disposed to receive at least some of the effluent of said chromatographic column and arranged to convert said sample to an analysis gas (that is, a gas comprising said sample in elemental form or in the form of a simple compound, eg nitrogen or carbon dioxide);

d) means for admitting into said mass spectrometer during at least one first time interval one or more calibration samples of a reference gas containing said element; and e) means for allowing carrier gas which has passed through said column to flow into said mass spectrometer only during at least one second time interval, outside the or each said first time interval, at least some of said analysis gas being allowed into said mass spectrometer during a second time interval.

In this form the invention further provides apparatus for carrying out the method previously described, and the criteria for the selection of the first and second time intervals are substantially identical to those described earlier.

Preferably, open-split means are provided for admitting only a portion of the effluent of the gas chromatographic column into the mass spectrometer and venting the remaining portion to a substantially constant, eg, atmospheric, pressure. Means may also be provided for adding a second flow of carrier gas prior to the conversion means, in which case the open-split means may conveniently be located between the conversion means and the mass spectrometer.

Means (typically a flow switching valve) may also be provided to control the flow of the effluent from the chromatographic column to the conversion means, thereby also controlling the admission of the converted sample into the mass spectrometer. Operation of this, and the valves for controlling the reference gas admission, is preferably by means of a computer which is programmed to admit the carrier gas and the reference gas according to the invention. The computer may also comprise means for integrating the outputs of the mass spectrometer as described previously.

In an embodiment adapted for the determination of the $^{13}C/^{12}C$ ratio in a carbon-containing sample, the sample is oxidized to an analysis gas comprising carbon dioxide in the conversion process. This may be done by means of a cupric oxide (CuO) catalyst maintained at 700–900°C., but other catalysts or oxidation processes may be used, eg platinum coated cupric oxide granules at 400–600°C.

If nitrogen is to be analyzed, the sample is preferably oxidized by a similar process. In practice, the nitrogen oxides formed usually undergo thermal decomposition to yield enough nitrogen gas to allow an accurate isotopic ratio to be determined by a method according to the invention, but if desired a second conversion stage may be used to reduce any remaining oxides to nitrogen, for example by means of heated copper. Other elements may also be determined using suitable conversion processes.

In a further preferred embodiment the apparatus of the invention additionally comprises a selective trapping means disposed between the sample conversion means and the spectrometer. Typically a cold trap is provided. The purpose of the trapping means depends on the element to be analyzed. In the case of carbon, the trapping means should be cooled sufficiently for water to be trapped but not enough to cause condensation of the carbon dioxide. In the case of nitrogen, it should remove both water and carbon dioxide because the latter yields mass spectrometric peaks at masses 28 and 29 which interfere with the nitrogen isotopic ratio measurements. Chemical traps (e.g, $MgClO_4$ for water) may also be used.

Figure 2:
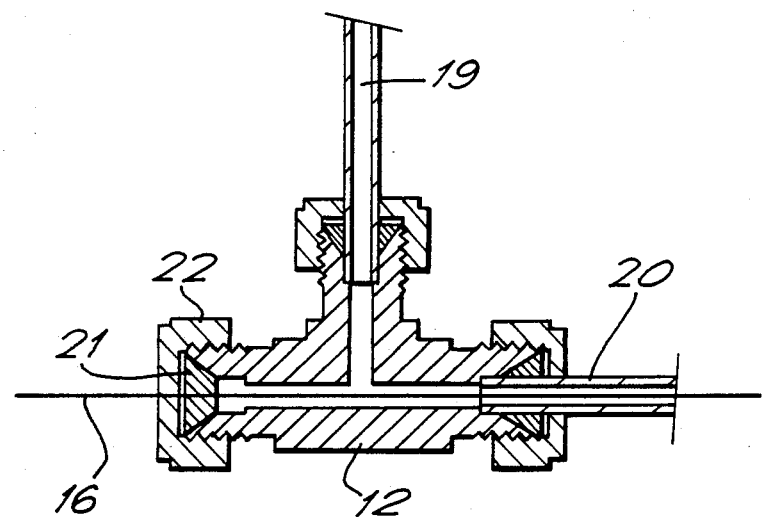

The invention will now be described in greater way of example and by reference to the figures, in which:

FIG. 1 is a schematic diagram of apparatus suitable for carrying out the method of the invention, and FIG. 2 is more detailed drawing of part of the apparatus shown in FIG. 1.

Referring first to FIG. 1, a sample containing the element to be analyzed is dissolved in a solvent contained in syringe 1. To start an analysis the solution in syringe 1 is injected through septum 2 into an injector 3 where it mixes with a flow of helium carrier gas 4 and is carried on to a gas chromatographic column 5. Column 5 is preferably a capillary column disposed inside a conventional gas chromatographic oven schematically shown at 6. Injector 3 is preferably also heated, either by the column oven 6 or a separate oven (not shown).

Column 5 terminates inside the oven in an effluent splitter 7 which, together with valve 10 provides means for admitting into the mass spectrometer during at least one second time interval gas which has passed through the column 5. Splitter 7 divides the flow between two routes 8 and 9. The flow along route 9 passes through a low-dead-volume valve 10 to a suitable chromatographic detector 11, typically a flame ionization detector. The flow along route 8 passes through a make-up tee 12, described in detail below, to a sample conversion means 17.

Splitter 7, valve 10, detector 11 and make-up tee 12 are all installed inside oven 6 so that they are maintained at the column operating temperature. Valve 10 is operated by a pneumatic actuator 13 located outside oven 6, and detector 11 is connected to a chart recorder or chromatograph data acquisition system 14.

After passing through detector 11, effluent flowing along route 9 passes through vent 15 to discharge at atmospheric pressure. When valve 10 is open, substantially all the column effluent will follow this route because the impedance it presents is very much less than the impedance presented by route 8 and the conversion means 17. Thus, by closing valve 10, column effluent is forced to flow through capillary 16 which is typically made of the same type of tubing as column 5 (e.g, 0.20 mm bore quartz capillary tube). Capillary 16 extends right through make-up tee 12 and into the sample conversion means 17, and a second flow of carrier gas 18 is introduced into tee 12 through pipe 19. An outlet pipe 20, typically 0.5 mm bore stainless steel, is fitted to the third port of the tee and extends part way into the body of the tee, as shown in FIG. 2. Capillary 16 is sealed into tee 12 by a graphitized ferrule 21 and secured by nut 22. Pipes 19 and 20 are sealed by conventional ferrules. Capillary 16 extends inside tube 20 so that the carrier gas entering through pipe 19 flows in the annular space between the exterior of capillary 16 and the inside wall of tube 20. This arrangement ensures turbulent mixing of the gases as they enter the sample conversion means 17.

Pipe 20 and capillary 16 are heated between oven 6 and the conversion means 17 by means of a heating oven (not shown) which maintains their temperature at least as high as the column temperature, thereby preventing condensation of the sample.

Sample conversion means 17 comprises a quartz tube 23, of 1.0 mm inside diameter and 40 cm length, which is packed with a catalyst 24. Pipe 20 is connected to tube 23 by means of a reducing coupling 26, through which capillary 16 extends into catalyst 24, which is capable of converting the element present in the sample into an analysis gas (defined above).

If carbon is to be determined, catalyst 24 may comprise cupric oxide or cobaltic oxide ($CuO$ or $Co_3O_4$) granules of 0.3–0.4 mm diameter. These materials are capable of oxidizing substantially all the carbon present in an organic sample to carbon dioxide when maintained at 700–900°C. Tube 23 is heated by an electrically heated furance 27 which surrounds tube 23. Other catalysts may be used if desired.

If nitrogen is to be determined, conversion means 17 may be adapted for the catalytic oxidation of nitrogen contained within the sample to nitrogen oxides, which may be achieved with cupric or cobaltic oxide as described above. Under these conditions, the nitrogen oxides formed usually undergo thermal decomposition to produce sufficient nitrogen for an accurate isotopic ratio determination. However, if desired a second stage for the reduction of the nitrogen oxides to gaseous nitrogen may be provided. Metallic copper may be used for this. In practice, both catalysts can be packed into tube 23. Obviously the inlet end will be packed with copper oxide and the exit end with copper. Separate tubes may be employed if desired.

Effluent from the tube 23, which now comprises the analysis gas (typically carbon dioxide) in the carrier gas (typically helium) passes through a reducing coupling 28 into pipe 29. An open split 30 is conveniently provided by ensuring that the inside diameter of coupling 28 is greater than the outside diameter of pipe 29, as shown. A small portion of the flow of analysis gas and carrier gas leaves tube 23 in pipe 29 and enters a coiled tube 33 in trapping means 32, which is adapted remove unwanted components such as water from the gas flow. Trapping means 32 comprises the coiled tube 33 in thermal contact with a thermally conductive bar 53. The other end of bar 53 is immersed in liquid nitrogen contained in an insulated vessel 34. The efficiency of the cooling of tube 33 is varied by means of a small electrical heater 31 mounted on bar 53, so that the temperature of tube 33 can be controlled by varying the power input to heater 31. For carbon isotope determination, the temperature should be maintained low enough to trap water but not carbon dioxide.

When carbon dioxide is to be removed, e.g, when nitrogen is being determined, the temperature of coiled tube 33 is reduced to condense carbon dioxide. Alternatively, additional chemical traps can be included.

The outlet of trapping means 32 is taken via a restriction 36 to one inlet of a conventional multi-collector isotope-ratio spectrometer 35, which has two inlet ports and a computerized data acquisition system 37. Restriction 36 is selected to limit the flow into the spectrometer to about 0.2–0.5 m/minute from atmospheric pressure (maintained by the splitting tee 30).

Valve 10 is operated at times such that analysis gas enters the mass spectrometer during one or more second time intervals, and preferably so that effluent from the column 5 passes into the conversion means 17 for substantially all of the time that a sample is eluting. In conjunction with the integration procedure described below, this ensures that errors due to isotopic fractionation of the sample during the chromatographic separation are minimized. Valve 10 should also be closed as soon as possible after the peak has passed into conversion means 17 to ensure that interference with a subsequent calibration sample from column bleed or an unwanted component of the sample entering conversion means 17 is minimized.

FIG. 1 also illustrates a preferred means for introducing into the mass spectrometer during at least one first time interval a calibration sample of a reference gas, such as a sample of carbon dioxide of accurately known isotopic composition. Reference gas flows in the direction of arrow 39 to pressure regulator 38 and a low-dead-volume valve 40 and through a capillary 42 into a second make-up tee 41. Tee 41 is of similar construction to tee 12, illustrated in FIG. 2. Capillary 42 extends from valve 40 through the tee 41 into a mixing volume provided by pipe 43, as shown in FIG. 1. Another flow of helium carrier gas 52 is supplied through regulator 45 into the side connection of the tee 41, which it leaves through the annular gap between the exterior of capillary 42 and the inside wall of mixing pipe 43. This arrangement ensures efficient mixing inside pipe 43 which is critically important if accurate calibration is to be achieved. Typically, for a carbon dioxide calibration system, capillary 42 comprises a 150 mm length of 0.025 mm inside diameter quartz tube and pipe 43 comprises a 150 mm length of 0.5 mm bore stainless steel tube. The diameter of the capillary 42 is much smaller than capillary 16 because only a very small flow of calibration gas is required. Efficient mixing can only be achieved, however, if a restriction exists downstream of pipe 43, and this is provided by a 200 mm length of 0.15 mm bore stainless steel capillary tube 44, connected to pipe 43 by coupling 46. Tube 44 terminates in coupling 47 and a short length of 0.5 mm bore tube 48 into which capillary 50 (typically 0.075 mm inside diameter) is introduced as shown in FIG. 1 to form an open split 49. Capillary 50, which typically is 1750 mm long, is connected to the second inlet of the mass spectrometer 35. Open split 49 and capillary 50 ensure that spectrometer 35 receives a constant flow of carrier gas from this source, irrespective of changes made upstream of split 49.

Calibration samples of reference gas are introduced during at least one first time interval simply by opening valve 40., which allows reference gas to enter the carrier gas flow into tee 41. The reference gas inlet comprising items 38-50 should have a very short response time which requires valve 40 to be of very low dead volume. Conveniently, valve 40 is operated by a pneumatic actuator 25. As explained, each first time interval is selected to be outside the or each second time interval, during which a sample of the analysis gas is present in the mass spectrometer.

The design of valves 10 and 40 has a very important effect on the performance of the system. They should start and stop the appropriate flows very quickly so that calibration samples and sample peaks can be introduced into the spectrometer in rapid succession and with minimum overlap. Micro needle valves of the type intended for use in gas chromatography in which the valve seat is integral with the ferrule sealing the outlet of the valve (for example type MOV from SGE Ltd) are suitable. In the case of valve 40, capillary 42 is secured in a conventional capillary ferrule with epoxy resin so that the end of the tube is about 1 mm from the valve seat. Such valves have a very small dead volume on the outlet side when closed.

A preferred method of operating the apparatus is as follows:

First, the interface system and a chromatographic column which will separate the components to be analyzed are conditioned in the normal way until a steady and small background signal is observed on the mass spectrometer. The sample is injected from syringe 1 on to the column 5 with valve 10 open so that column effluent is routed through the detector 11 and subsequently vented. Meanwhile, one or more calibration samples may be admitted into the mass spectrometer by opening valve 40. The isotopic composition of these is measured in a conventional way.

Once the solvent and any unwanted components prior to the peak to be analyzed have eluted from column 5, valve 10 is closed to allow substantially all of the peak to pass into the conversion means 17 where it is converted to a gas (e.g, $CO_2$ or $N_2$) suitable for admission into the mass spectrometer. Selective trapping means 32 removes water and other unwanted material from the effluent of the conversion means, which is then admitted into the spectrometer. The isotopic ratio of the element under investigation is then determined by integrating with respect to time the outputs of the mass spectrometer which are indicative of at least two isotopes of the element. This should be carried out over the entire chromatographic peak to ensure that fractionation effects during the chromatograph separation or conversion do not adversely affect the measurement.

As soon as substantially all of the converted sample has been analyzed, valve 10 is closed and more calibration samples are admitted by opening valve 40. The isotopic composition of the sample is determined using the results of the calibration sample in a conventional way.

If the sample in syringe 1 is a mixture, other components eluting from the column may be analyzed during a single run, interspersing calibration samples between the peaks whenever possible. If the time between two peaks is too short to allow a calibration sample to be inserted, these peaks may be analyzed consecutively using calibration samples analyzed on either side of the pair.

It will be appreciated that the whole apparatus is preferably automated and under the control of the computerized data acquisition system 37, which is also programmed to carry out the integration as discussed above. The acquisition system 37 may also conveniently be programmed to control valves 10 and 40, and also an automatic injector if available, to admit the sample to be analyzed and calibration samples according to the invention making due allowance for the time delays introduced by the column 5 and the conversion means 17, which are determined by previous experiments. Automation of the remainder of the system is conventional and need not be described in detail.

What is claimed is:

1. A method of determining the isotopic composition of an element comprised in a sample, said method comprising the steps of:
    a) passing a carrier gas through a gas chromatographic column and introducing said sample in to the column;
    b) converting at least some of said sample present in the effluent from the column into an analysis gas comprising said element in elemental form or in the form of a simple compound;
c) introducing at least one calibration sample of a reference gas containing said element into a mass spectrometer during at least one first time interval;
d) allowing carrier gas which has passed through the column to flow into the mass spectrometer only during at least one second time interval, at least some of said analysis gas being allowed into the mass spectrometer during a said second time interval, said first and second time intervals being non-overlapping; and
e) determining the isotopic composition of said element in said analysis gas from outputs of the mass spectrometer indicative of said element in said analysis gas and said reference gas.

2. A method according to claim 1 in which only some of the effluent from said gas chromatographic column is introduced into the mass spectrometer during said second time intervals and the remaining portion is vented at a substantially constant pressure.

3. A method according to claim 2 in which a second flow of a carrier gas is added to the effluent from said column prior to the conversion of said sample into said analysis gas.

4. A method according to claim 1 in which at least one of said second time intervals is selected so that:
a) at least some of said effluent from said chromatographic column is converted into said analysis gas for substantially all of the time said sample is present in it;
b) at least some of the effluent after conversion is passed into said mass spectrometer for substantially all of the time said analysis gas is present in it; and
c) said isotopic composition is determined in part by integration of the outputs of said mass spectrometer indicative of at least two isotopes of said element in said analysis gas for substantially all of the time said analysis gas is entering said mass spectrometer.

5. A method according to claim 1 in which effluent from said gas chromatographic column is passed into means for converting said sample into said analysis gas only during the time in which a sample whose isotopic composition is to be determined is eluting from said chromatographic column.

6. A method according to claim 2 in which effluent from said gas chromatographic column is passed into means for converting said sample into said analysis gas only during the time in which a sample whose isotopic composition is to be determined is eluting from said chromatographic column.

7. A method according to claim 4 in which effluent from said gas chromatographic column is passed into means for converting said sample into said analysis gas only during the time in which a sample whose isotopic composition is to be determined is eluting from said chromatographic column.

8. The method of claim 1 wherein said element is carbon and said analysis gas comprises carbon dioxide.

9. The method of claim 1 wherein said element is nitrogen and said analysis gas comprises nitrogen.

10. The method of claim 2 in which said substantially constant pressure is atmospheric pressure.

11. Apparatus for determination of the isotopic composition of an element comprised in a sample, said apparatus comprising:
a) an isotopic ratio mass spectrometer, said spectrometer determining the isotopic composition of an element comprised in a gas;
b) a gas chromatographic column through which a sample may be passed together with a carrier gas;
c) sample conversion means disposed to receive at least some of the effluent of said chromatographic column, said conversion means converting said sample to an analysis gas comprising said sample in elemental form or in the form of a simple compound;
d) means for admitting into said mass spectrometer during at least one first time interval at least one calibration sample of a reference gas containing said element; and
e) means for allowing carrier gas which has passed through said column to flow into said mass spectrometer only during at least one second time interval, at least some of said analysis gas being allowed into said mass spectrometer during a said second time interval, said first and second time intervals being non-overlapping.

12. Apparatus according to claim 11 wherein said means for allowing flow into said mass spectrometer comprises flow splitter means for admitting only a selected portion of said effluent from said chromatographic column into said mass spectrometer and for venting the remainder of said effluent at a substantially constant pressure.

13. Apparatus according to claim 12 in which said splitter means is an open-splitter disposed downstream of said sample conversion means and further comprising means for adding a second flow of a carrier gas to the effluent of said chromatographic column at the entrance to said sample conversion means.

14. Apparatus according to claim 11 wherein said means for allowing carrier gas to flow into said mass spectrometer allows the effluent from said chromatographic column to pass into said sample conversion means only during a period in which said sample is eluting from said chromatographic column.

15. Apparatus according to claim 13 wherein said means for allowing carrier gas to flow into said mass spectrometer allows the effluent from said chromatographic column to pass into said sample conversion means only during a period in which said sample is eluting from said chromatographic column.

16. Apparatus according to claim 11 in which said means for allowing carrier gas to flow into said mass spectrometer during at least one second time interval causes at least some of the effluent from said chromatographic column to pass into said sample conversion means for substantially all of the time said sample is present in the effluent from said chromatographic column, at least some of the effluent from said sample conversion means being passed into said mass spectrometer for substantially all of the time that said analysis gas is present in the effluent from said conversion means, and means are provided for intergrating with respect to time the output of said mass spectrometer indicative of at least two isotopes of said element for substantially all of the time that said analysis gas is entering said mass spectrometer.

17. Apparatus according to claim 16 wherein said means for allowing carrier gas to flow into said mass spectrometer allows the effluent from said chromatographic column to pass into said sample conversion means only during a period in which said sample is eluting from said chromatographic column.

18. Apparatus according to claim 11 in which said element comprises carbon and said analysis gas and said reference gas comprise carbon dioxide.

19. Apparatus according to claim 14 in which said element comprises carbon and said analysis gas and said reference gas comprise carbon dioxide.

20. Apparatus according to claim 16 in which said element comprises carbon and said analysis gas and said reference gas comprise carbon dioxide.

21. Apparatus according to claim 11 further comprising trapping means disposed between said sample conversion means and said mass spectrometer to remove condensable impurities from the effluent of said sample conversion means.

22. Apparatus according to claim 14 further comprising trapping means disposed between said sample conversion means and said mass spectrometer to remove condensable impurities from the effluent of said sample conversion means.

23. Apparatus according to claim 16 further comprising trapping means disposed between said sample conversion means and said mass spectrometer to remove condensable impurities from the effluent of said sample conversion means.

24. The apparatus of claim 12 wherein said substantially constant pressure is atmospheric pressure.

* * * * *